US008680303B2

(12) United States Patent  (10) Patent No.: US 8,680,303 B2
Jamison et al.  (45) Date of Patent: Mar. 25, 2014

(54) EPOXIDATION CATALYSTS (75) Inventors: Timothy F. Jamison, Somerville, MA (US); Yutaka Ikeuchi, Brookline, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 387 days.

(21) Appl. No.: 13/037,060

(22) Filed: Feb. 28, 2011

(65) Prior Publication Data

US 2011/0257415 A1  Oct. 20, 2011

(51) Int. Cl.
*C07D 317/00* (2006.01)

(52) U.S. Cl.
USPC .......................................... 549/453; 549/454

(58) Field of Classification Search
USPC ................................................ 549/453, 454
See application file for complete search history.

(56) References Cited

U.S. PATENT DOCUMENTS

| | | | |
|---|---|---|---|
| 3,960,973 | A | 6/1976 | Stapp |
| 4,126,751 | A | 11/1978 | Stapp |
| 6,252,113 | B1 | 6/2001 | Palmer et al. |
| 6,645,432 | B1 | 11/2003 | Anderson et al. |
| 8,314,246 | B2 | 11/2012 | Jamison et al. |
| 2005/0107635 | A1 | 5/2005 | Mehra et al. |
| 2005/0245628 | A1 | 11/2005 | Hubel et al. |
| 2007/0073068 | A1 | 3/2007 | Quaedflieg et al. |
| 2007/0197801 | A1 | 8/2007 | Bolk et al. |
| 2011/0118469 | A1 | 5/2011 | Bedore et al. |

FOREIGN PATENT DOCUMENTS

| | | |
|---|---|---|
| IN | 177748 A1 | 2/1997 |
| WO | WO 95/25104 A1 | 9/1995 |
| WO | WO 98/22426 A1 | 5/1998 |
| WO | WO 00/75114 A1 | 12/2000 |
| WO | WO 2004/076422 A1 | 9/2004 |
| WO | WO 2005/037819 A1 | 4/2005 |
| WO | WO 2005/123684 A2 | 12/2005 |
| WO | WO 2006/023457 A1 | 3/2006 |
| WO | WO 2007/141593 A2 | 12/2007 |
| WO | WO 2008/028586 A1 | 3/2008 |
| WO | WO 2008/068927 A1 | 6/2008 |

OTHER PUBLICATIONS

Ramasastry et al Org. Lets. vol. 10 No. 8 pp. 1621-1624 (2008).*
Molas et al, J. Org. Chem. vol. 70 (2005) pp. 10143-10146.*
Zhao et al, DN 145:189088.*
International Search Report and Written Opinion for PCT/US2006/033829 mailed Feb. 1, 2007.
International Preliminary Report on Patentability for PCT/US2006/033829 mailed Mar. 4, 2008.
International Search Report and Written Opinion for PCT/US2010/055386 mailed Mar. 23, 2011.
International Preliminary Report on Patentability for PCT/US2010/055386 mailed May 18, 2012.
Invitation to Pay Additional Fees for PCT/US2011/026439 mailed Apr. 28, 2011.

(Continued)

*Primary Examiner* — Andrew D Kosar
*Assistant Examiner* — Raymond Covington
(74) *Attorney, Agent, or Firm* — Wolf, Greenfield & Sacks, P.C.

(57) ABSTRACT

The present invention generally relates to methods for the synthesis of catalysts, including epoxidation catalysts, and related compounds and catalyst compositions. Embodiments described herein may provide efficient processes for providing catalysts (e.g., epoxidation catalysts) in large quantities and using simplified methods.

25 Claims, 2 Drawing Sheets

(56) References Cited

OTHER PUBLICATIONS

International Search Report and Written Opinion for PCT/US2011/026439 mailed Jul. 11, 2011.
International Preliminary Report on Patentability for PCT/US2011/026439 mailed Sep. 13, 2012.
[No Author Listed] Microreactiors find new niches. Chemical Engineering, Access Intelligence Association, Rockville, MA. Mar. 1, 1997:30-1,33.
Adams et al., "The Prins Reaction," *Synthesis* 1977, 661-672.
Ager et al., An Epoxidation Approach to a Chiral Lactone: Application of the Shi Epoxidation. J Org Proc Rev Dev. 2007;11:44-51.
Anderson et al., The preparation of β-substituted amines from mixtures of epoxide opening products via a common aziridinium ion intermediate. Tetrahedron: Asymmetry 1999, 10, 2655-63.
Arundale, E. et. al., "The Olefin-Aldehyde Condensation: The Prins Reaction," *Chem. Rev.* 1953, 52, 505-555.
Azizi et al., Highly Chemoselective Addition of Amines to Epoxides in Water. *Org. Lett.* 2005, 7,3649-51.
Bach et al., Photochemical deconjugation of chiral 3-methyl-2-butenoates derived from carbohydrate-based alcohols: the influence of the sugar backbone on the facial diastereoselectivity. J Org Chem. May 18, 2001;66(10):3427-34.
Bedore et al., Aminolysis of Epoxides in a Microreactor system: a continuous flow approach to β-Amino alcohols. Org Process Res Dev. 2010;14(2):432-40.
Beessieres et al., Iodomethyl group as a hydroxymethyl synthetic equivalent: application to the syntheses of D-manno-hept-2-ulose and 1-fructose derivatives. J Org Chem. May 16, 2003;68(10):4100-3.
Benito-Lopez et al., High pressure in organic chemistry on the way to miniaturization. *Tetrahedron* 2008, 64, 10023-40.
Bergmeier, The Synthesis of Vicinal Amino Alcohols. Tetrahedron 2000, 56, 2561-76.
Bonollo et al., A green route to β-amino alcohols via the uncatalyzed aminolysis of 1,2-epoxides by alkyl- and arylamines. *Green Chem.* 2006, 8,960-4.
Bowman et al., Approaches for Scale-Up of Microwave-Promoted Reactions. A. *Org. Process Res. Dev.* 2008, 12,41-57.
Bowman et al., Scale-Up of Microwave-Promoted Reactions to the Multigram Level Using a Sealed-Vessel Microwave Apparatus. *Org. Process Res. Dev.* 2008, 12,1078-88.
Brady JR, Cyclic acetals of ketoses ☆: Part III. Re-investigation of the synthesis of the isomeric DI-O-isopropylidene-β-d-fructopyranoses. Carbohydro Res. 1970;15:35-40.
Brandsma et al., "The first successful direct metallation of ethene," J. Chem. Soc., Chem. Comm. 1986, 260-1.
Budnik et al., Epoxidation of olefins with molecular oxygen in the presence of cobalt complexes. J Org Chem. 1976;41:1386.
Cepanec et al., Calcium trifluoromethanesulfonate-catalysed aminolysis of epoxides. Tetrahedron, 2003, 59, 2435.
Chini et al., Lanthanide(III) trifluoromethanesulfonates as extraordinarily effective new catalysts for the aminolysis of 1,2-epoxides *Tetrahedron Lett.* 1994, 35, 433.
Córdova et al., Direct organocatalytic aldol reactions in buffered aqueous media. Chem Commun (Camb). Dec. 21, 2002;(24):3024-5.
Cossy et al., Regioselective ring opening of epoxides by nucleophiles mediated by lithium bistrifluoromethanesulfonimide. *Tetrahedron Lett.* 2002,43,7083.
Couturier et al., Efficient synthesis of the κ-opioid receptor agonist CJ-15,161: four stereospecific inversions at a single aziridinium stereogenic center. Tetrahedron Asymmetry. Nov. 14, 2003;14(22):3517-23.
Crowe et al., "Titanium-Catalyzed Reductive Cyclization of d,e-Unsaturated Ketones and Aldehydes," *J. Am. Chem. Soc.* 1995, 117, 6787-8.
Desai et al., Regioselectivity in a Highly Efficient, Microwave-Assisted Epoxide Aminolysis. *Synthesis* 2007, 902.
Enders et al., Direct organocatalytic de novo synthesis of carbohydrates. Ang Chem Int Ed. 2005;44:1210.

Fayet et al., Synthesis of 3-substituted furans from 3-C-substituted hexuloses. Carbohydro Res. Nov. 1, 1986;155:99-106.
Glasnov et al., Microwave-Assisted Synthesis under Continuous-Flow Conditions. *Macromol. Rapid Commun.* 2007,28,395-410.
Goodell et al., Development of an Automated Microfluidic Reaction Platform for Multidimensional Screening: Reaction Discovery Employing Bicyclo[3.2.1]octanoid Scaffolds. J. Org. Chem. 2009;74(16):6169-80.
Hayashi, M., "Fluoride-catalyzed three-component coupling reaction of a silylphosphine, activated alkenes and aldehydes," *Tet Lett.* 2005, 46, 5135-5138.
Ho et al., Nickel-catalyzed, carbonyl-ene-type reactions: selective for aplha olefins and more efficient with electron-rich aldehydes. J Am Chem Soc. 2006;128:5632-3.
Huang et al., "Highly Selective Catalytic Intermolecular Reductive Coupling of Alkynes and Aldehydes," *Org. Lett.* 2000, 2, 4221-4223.
Jang et al., "Hydrogen-Mediated C—C Bond Formation: Catalytic Regio- and Stereoselective Reductive Condensation of α-Keto Aldehydes and 1,3-Enynes," *J. Am. Chem. Soc.* 2004, 126, 4664-4668.
Jang et al., "Reductive Generation of Enolates from Enones Using Elemental Hydrogen: Catalytic C—C Bond Formation under Hydrogenative Conditions," *J. Am. Chem. Soc.* 2002, 124, 15156-15157.
Jang et al., A New catalytic C[bond]C bond-forming hydrogenation: reductive coupling of dienes and glyoxals under catalytic hydrogenation conditions. *Angew. Chem. Int. Ed.* 2003, 42, 4074-4077.
Jas et al., Continuous Flow Techniques in Organic Synthesis. *Chem. Eur. J.* 2003, 9, 5708-23.
Jensen, Silicon-Based Microchemical Systems: Characteristics and Applications. *Mater. Res. Soc. Bull.* 2006, 31, 101-7.
Johnson et al., Numerical studies of steady flow dispersion at low Dean number in a gently curving tube. J Fluid Mechanics Digital Archive. 1986;172(-1):329-45.
Kablaoui et al., "Reductive Cyclization of Enones by a Titanium Catalyst," *J. Am. Chem. Soc.* 1995, 117, 6785-6786.
Kappe et al., Controlled Microwave Heating in Modern Organic Synthesis. *Angew. Chern. Int. Ed.* 2004, 43, 6250-84.
Kimura et al., "Novel and Highly Regio- and Stereoselective Nickel-Catalyzed Homoallylation of Benzaldehyde with 1,3-Dienes," *J. Am. Chem. Soc.* 1998, 120, 4033-4034.
Kravchenko et al., The effect of solvents on the rate of the aminolysis reactions of substituted α-oxides. Ukrainian Chemistry Journal. 1990;56(2):168-72.
Kumar et al., Phosphomolybdic acid-Al2O3: A mild, efficient, heterogeneous and reusable catalyst for regioselective opening of oxiranes with amines to β-amino alcohols. J. *Mol. Catal. A: Chern.* 2007, 266, 65.
Maheswara et al., Regioselective ring-opening of epoxides with amines using Zn(ClO4)2—Al2O3 as a heterogeneous and recyclable catalyst. *Tetrahedron Lett.* 2008, 49,1795.
Majewski et al., Stereoselective Synthesis of Protected Ketohexoses via Aldol Reaction of Chiral Dioxanone Enolate. Synlett. 1999;1999(9):1447-9.
Markert et al., Amine-catalyzed direct aldol addition. J Am Chem Soc. 2007;129:7258-9.
Marriner et al., "Metallo-Aldehyde Enolates via Enal Hydrogenation: Catalytic Cross Aldolization with Glyoxal Partners As Applied to the Synthesis of 3,5-Disubstituted Pyridazines," *J. Org. Chem.* 2003, 69, 1380-1382.
Maryanoff et al., Synthesis of phosphates and phosphate isosteres of furanose sugars as potential enzyme inhibitors. Tetrahedron. 1988;44:3093.
Mason et al., Greener Approaches to Organic Synthesis Using Microreactor Technology. Chem. Rev. 2007,107,2300-18.
Matsuda et al., Rhodium catalyzed direct coupling of αβ-unsaturated ketone, aldehyde, and trialkylsilane: An easy access to regio-defined aldol derivatives. *Tetrahedron Lett.* 1990, 31, 5331-5334.
McDonald., A new synthesis of d-psicose (d-ribo-hexulose). Carbohydro Res. 1967;5:106-8.
Miller et al., "Catalytic Asymmetric Reductive Coupling of Alkynes and Aldehydes: Enantioselective Synthesis of Allylic Alcohols and α-Hydroxy Ketones," *J. Am. Chem. Soc.* 2003, 125, 3442-3443.

(56) References Cited

OTHER PUBLICATIONS

Mio et al., Synthetic studies on (+)-hydantocidin (3): a new synthetic method for construction of the spiro-hydantoin ring at the anomeric position of D-ribofuranose. Tetrahedron. 1991;47(12-13):2133-44.
Montgomery, J., Nickel-catalyzed reductive cyclizations and couplings. *Angew. Chem. Int. Ed.* 2004, 43, 3890-3908.
Morgenlie, Synthesis of Di-O-Isopropylidene derivates of L-fructose. Carbohydrate Res. 1982;107:137-41.
Moseley et al., Scaling-Out Pharmaceutical Reactions in an Automated Stop-Flow Microwave Reactor. *Org. Process Res. Dev.* 2008, 12,967-81.
Murphy et al., Accelerating Reactions with Microreactors at Elevated Temperatures and Pressures: Profiling Aminocarbonylation Reactions. *Angew. Chem. Int. Ed.* 2007,46, 1734-7.
Myint et al., Temperature-dependent diffusion coefficient of soluble substances during ethanol extraction of clove. J American Oil Chemists' Soc. 1996;73(5):603-10.
Ng et al., "Highly Enantioselective and Regioselective Nickel-Catalyzed Coupling of Allenes, Aldehydes, and Silanes," *J. Am. Chem. Soc.* 2005, 127, 7320-7321.
Ng et al., "Nickel-Catalyzed Coupling of Alkenes, Aldehydes, and Silyl Triflates," *J. Am. Chem. Soc.* 2006, 128, 11513-11528, as published online Aug. 10, 2006.
Ng et al.., "Simple Alkenes as Substitutes for Organometallic Reagents: Nickel-Catalyzed, Intermolecular Coupling of Aldehydes, Silyl Triflates, and Alpha Olefins," *J. Am. Chem. Soc.* 2005, 127(41), 14194-5.
Niu et al., Enantioselective Total Syntheses of [6R,7R] and [6S,7S] Tricyclic β-Lactams. J Org Chem. 1996;61(3):1014-22.
Oblinger et al., "A New Stereoselective Method for the Preparation of Allylic Alcohols," *J. Am. Chem. Soc.* 1997, 119, 9065-9066.
Oblinger, E. S., "Nickel-Catalyzed and Organozinc-Mediated Carbocyclizations and Three-Component Couplings," (Ph.D. Thesis, Wayne State University, 1997), 88 pages.
Ogoshi et al., "AlMe$_3$-Promoted Oxidative Cyclization of $h^2$-Alkene and $h^2$-Ketone on Nickel(0). Observation of Intermediate in Methyl Transfer Process," *J. Am. Chem. Soc.* 2005, 127(37), 12810-12811.
Ogoshi et al., "Direct Observation of Oxidative Cyclization of $h^2$-Alkene and $h^2$-Aldehyde on Ni(0) Center. Significant Alteration by Addition of Me$_3$-SiOTf," *J. Am. Chem. Soc.* 2004, 126(38), 11802-3.
Onaka et al., Zeolite-catalyzed ring-opending of epoxides with amines. *Chem. Lett.* 1985;6:779-82.
Schmid et al., D-(R)-glyceraldehyde acetonide. Org Synth 1998;9:450.
Parker et al., Mechanisms of Epoxide Reactions. Chem. Rev. 1959;59(4):737-99.
Prashad et al., An Efficient and Economical Synthesis of 5,6-Diethy1-2,3-dihydro-1H-inden-2-amine Hydrochloride. J. *Org. Process Res. Dev.* 2006, 10,135-41.
Procopio et al., Highly efficient and versatile chemoselective addition of amines to epoxides in water catalyzed by erbium(III) triflate. *Tetrahedron Lett.* 2008,49,2289.
Ramón et al., Asymmetric multicomponent reactions (AMCRs): the new frontier. *Angew. Chem. Int. Ed.* 2005, 44, 1602-1634.
Revis et al., Novel synthesis of β-siloxy esters by condensation of carbonyls and trimethylsilane with α,β-unsaturated esters catalyzed by RhC13. *Tetrahedron Lett.* 1987, 28, 4809-4812.
Roberge et al., Microreactor Technology and Continuous Processes in the Fine Chemical and Pharmaceutical Industry: Is the Revolution Underway? *Org. Process Res. Dev.* 2008, 12, 905-10.
Rogers et al., Comparative chemistry of the bay- and non-bay-region tetrahydro epoxides of phenanthrene. J. Am. Chem. Soc. 1979;101(16):4713-4719.
Sato et al., "Nickel-Catalyzed Intermolecular Coupling of 1,3-Dienes and Aldehydes via Transmetalation of Nickelacycles with Diisobutylaluminum Acetylacetonate," *J. Org. Chem.* 2002, 67, 656-662.

Shi et al., Synthesis of 1,2:4,5-di-o-isopropylidene-d-erythro-2,3-hexodiulo-2,6-pyranose. a highly enantioselective ketone catalyst for epoxidation Org Synth. 2003;80:1.
Shi et al., Practical synthesis of an 1-fructose-derived ketone catalyst for asymmetric epoxidation of olefins.J Org Chem. 2006;71:5377-9.
Shibuya et al., 2-Azaadamantane N-Oxyl (AZADO) and 1-Me-AZADO: Highly Efficient Organocatalysts for Oxidation of Alcohols. J Am Chem Soc. 2006;128(26):8412-3.
Sirovski et al., Large-scale fatty amine ethoxylation reactor: A dynamic model. Chemical Engineering Journal. 2006;117(3):197-203.
Sodeoka et al., New method for the stereocontrolled synthesis of silyl dienol ethers using (naphthalene)chromium tricarbonyl catalyzed isomerization. J Am Chem Soc. 1990;112(12): 4906-4911.
Sturton et al., Pharmacological Characterization of Indacaterol, a Novel Once Daily Inhaled β2 Adrenoceptor Agonist, on Small Airways in Human and Rat Precision-Cut Lung Slices. *J. Pharmacol. Exp. Ther.* 2008, 324, 270-5.
Sudarsanet al., Multivortex micromixing. PNAS. 2006;103(19):7228-33.
Sundaram et al., Kinetics of reactions of amines with alkene oxides. Bulletin of the Chemical Society of Japan. 1969;42(11):3141-7.
Takai et al., "Regioselective Reductive Coupling of Alkynes and Aldehydes Leading to Allylic Alcohols," *Org. Lett.* 2003, 5, 653-656.
Taylor et al., "Catalytic Diastereoselective Reductive Aldol Reaction: Optimization of Interdependent Reaction Variables by Arrayed Catalyst Evaluation," *J. Am. Chem. Soc.* 1999, 121, 12202-12203.
Tian et al., Electronic probing of ketone catalysts for asymmetric epoxidation. Search for more robust catalysts. Org Lett. Mar. 8, 2001;3(5):715-8.
Tipson et al., Cyclic acetals of ketoses : Part IV. Re-investigation of the oxidation of 1,2:4,5-DI-O-isopropylidene-β-D-fructopyranose with methyl sulfoxide—acetic anhydride. Carbohydro Res. Feb. 2, 1971;16(2):383-93.
Trejbal et al., Kinetics of ethylenediamine and piperazine ethoxylation. Reaction Kinetics and Catalysis Lett. 2004;82(2):339-46.
Trost et al., "Non-metathesis ruthenium-catalyzed C-C bond formation," *Chem. Rev.* 2001, 101, 2067-2096.
Tsujimoto, S., "Addition of aldehydes and their equivalents to electron-deficient alkenes using N-hydroxyphthalimide (NHPI) as a polarity-reversal catalyst," *Tet Lett.* 2003, 44, 5601-5604.
Tu et al., An Efficient Asymmetric Epoxidation Method for trans-Olefins Mediated by a Fructose-Derived Ketone. J Am Chem Soc. 1996;118:9806-7.
Utsumi et al., Mimicking aldolases through organocatalysis: syn-selective aldol reactions with protected dihydroxyacetone. Org Lett. 2007;9:3445-8.
Vijender et al., Amberlist-15 as heterogeneous reusable catalyst for regioselective ring opening of epoxides with amines under mild conditions. *J. Mol. Catal. A: Chern.* 2007, 266, 290.
Vinnik et al., Kinetic Method by Using Calorimetry to Mechanism of Epoxy-Amine Cure Reaction; Part II. On catalytic action of the amine excess. Journal of Thermal Analysis and Calorimetry. 2003;73:819-26.
Vinnik et al., Kinetic Method by Using Calorimetry to Mechanism of Epoxy-Amine Cure Reaction; Part V. Phenyl glycidyl ether—aniline Journal of Thermal Analysis and Calorimetry. 2004;75:753-64.
Vinnik et al., Kinetic Method by Using Calorimetry to Mechanism of Epoxy-Amine Cure Reaction; Part I. Mangeldorf's Approach. Journal of Thermal Analysis and Calorimetry. 2003;73:807-17.
Voisin-Chiret et al., Synthesis of new L-ascorbic ferulic acid hybrids. Molecules. Nov. 17, 2007;12(11):2533-45.
Waagstein et al., Beneficial effects of metoprolol in idiopathic dilated cardiomyopathy. *Lancet* 1993;342(8885):1441-6.
Wang et al., An efficient catalytic asymmetric epoxidation method. J Am Chem Soc. 1997;119(46):11224-35.
Wender et al., "Bis(1.5-cyclooctadiene)nickel(0)," Encyclopedia of Reagents for Organic Synthesis, Article Online Posting Date: Sep. 15, 2006, 44 pages.
Wender et al., CAS: 149:30799, 2001.
Wiles et al., Continuous Flow Reactors, a Tool for the Modern Synthetic Chemist. *Eur. J. Org. Chern.* 2008, 1655-71.

(56) References Cited

OTHER PUBLICATIONS

Wiles et al., Improving chemical synthesis using flow reactors. *Expert Opin. Drug Discovery* 2007, 2, 1487-503.
Wong et al., Organocatalytic oxidation. Asymmetric epoxidation of olefins catalyzed by chiral ketones and iminium salts. Chem Rev. Sep. 2008;108(9):3958-87. Epub Jul. 1, 2008.
Yadav et al., An efficient protocol for regioselective ring opening of epoxides using samarium triflate: Synthesis of propranolol, atenolol and RO363. Mol. Catal. A: Chem. 2007,261,207.
Zaborenko et al., Synthesis and Kinetics of highly energetic intermediates by micromixers: direct multistep synthesis of sodium nitrotetrazolate. Industrial & Engineering Chem Res. 2010;49(9):4132-9.
Zaborenko et al., Kinetic and Scale-Up Investigations of Epoxide Aminolysis in Microreactors at High Temperatures and Pressures. Organic Process Research & Development. 2011;15:131-9.
Koch et al., Enzymatic enantioselective C-C-bond formation in microreactors. Biotechnol Bioeng. Mar. 1, 2008;99(4):1028-33.
Sugimoto et al., The Barton reaction using a microreactor and black light. Continuous-flow synthesis of a key steroid intermediate for an endothelin receptor antagonist. Tetrahedron Lett. Aug. 28, 2006;47(35):6197-6200.
Yamashita et al., Thermodynamic properties of duplex DNA in microchannel laminar flow. Chemphyschem. Jun. 25, 2007;8(9):1307-10.

\* cited by examiner

EPOXIDATION CATALYSTS

STATEMENT REGARDING FEDERALLY SPONSORED RESEARCH OR DEVELOPMENT

This invention was made with government support under Grant No. R01 GM072566 awarded by the National Institutes of Health. The government has certain rights in this invention.

RELATED APPLICATIONS

This application claims priority under 35 U.S.C. §119(e) to co-pending U.S. Provisional Application Ser. No. 61/309,067, filed Mar. 1, 2010, the contents of which are incorporated herein by reference in its entirety for all purposes.

FIELD OF THE INVENTION

The present invention generally relates to methods for the synthesis of catalysts, including epoxidation catalysts, and related compositions.

BACKGROUND OF THE INVENTION

Optically active epoxides provide useful building blocks in the synthesis of many biologically active compounds, and much research has been conducted on practical, efficient methods for the synthesis of such epoxides. For example, numerous catalysts have been developed to perform epoxidation reactions, in which an alkene is converted to an epoxide by addition of one oxygen atom to a carbon-carbon double bond. In particular, the "Shi Epoxidation," is an enantioselective epoxidation method developed by Prof. Yian Shi and coworkers, which utilizes Shi catalyst 1, shown below.

1

While the Shi Epoxidation method has been shown to be effective for enantioselective epoxidation reactions, to date, Shi catalyst 1 can only be produced in large quantities as one enantiomer. The absence of the availability of the enantiomer of Shi catalyst 1 has hindered the more widespread use of the Shi Epoxidation.

SUMMARY OF THE INVENTION

The present invention provides methods for synthesizing a catalyst. In one set of embodiments, the method comprises reacting a compound of Formula (I), wherein:

$R^1$ and $R^2$ can be the same or different and each can be hydrogen, alkyl, or aryl, provided that when one of $R^1$ and $R^2$ is hydrogen, the other is alkyl or aryl;

$R^3$ is a protecting group;

$R^4$ is a protecting group that can be removed in the presence of an acid; and $R^5$, $R^6$, $R^7$, and $R^8$ can be the same or different and each can be hydrogen, alkyl, or aryl, to produce a compound of Formula (II), The present invention also relates to compositions comprising a compound having a structure as in Formula (I):

wherein:

$R^1$ and $R^2$ can be the same or different and each can be hydrogen, alkyl, or aryl, provided that when one of $R^1$ and $R^2$ is hydrogen, the other is alkyl or aryl;

$R^3$ is a protecting group;

$R^4$ is a protecting group that can be removed in the presence of an acid; and $R^5$, $R^6$, $R^7$, and $R^8$ can be the same or different and each can be hydrogen, alkyl, or aryl.

The present invention also relates to compositions comprising a compound having a structure as in Formula (II):

(II)

wherein:

$R^1$ and $R^2$ can be the same or different and each can be hydrogen, alkyl, or aryl, provided that when one of $R^1$ and $R^2$ is hydrogen, the other is alkyl or aryl; and $R^5$, $R^6$, $R^7$, and $R^8$ can be the same or different and each can be hydrogen, alkyl, or aryl.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally relates to methods for the synthesis of catalysts, including epoxidation catalysts, and related compounds and catalyst compositions. Some embodiments provide methods for synthesizing large amounts (e.g., greater than 10 grams) of a catalyst composition that may otherwise be difficult to obtain using known methods. In some embodiments, compounds and intermediates useful in the synthesis of catalysts are provided. Embodiments described herein may provide efficient processes for providing catalysts (e.g., epoxidation catalysts) in large quantities and using simplified methods.

Methods for synthesizing the compounds and catalyst compositions described herein are provided. In some cases, the method may comprise reacting an intermediate molecule to produce a compound or catalyst, as described herein. In some cases, the intermediate molecule may be a compound comprising at least one ketal group and/or at least one protecting group. Other intermediate molecules are described herein, including the Examples. Methods described herein may involve one or more chemical transformations, which may be performed sequentially and/or simultaneously. For example, the method may comprise reacting a compound in the presence of a chemical reagent (e.g., acid), wherein multiple chemical transformations may occur in a single reaction step. Those of ordinary skill in the art would be able to select the appropriate set(s) of reaction conditions (e.g., concentration, temperature, pressure, reaction time, solvents, etc.) suitable for use in a particular application. In some cases, the method may further comprise isolating and/or purifying the compound and/or catalyst, for example, by chromatography (e.g., column chromatography, HPLC), crystallization, precipitation, distillation, filtration, solvent extraction, and the like. The method may also comprise characterization of the compound and/or catalyst by mass spectrometry, NMR, and the like.

Some embodiments relate to the synthesis of the following compound, also known as the "ent-Shi ketone" catalyst, which is the enantiomer of a commercially available catalyst known as "Shi ketone." The ent-Shi ketone catalyst has been shown to be an effective catalyst for enantioselective epoxidation reactions. In some embodiments, methods for synthesizing the ent-Shi ketone catalyst, as described herein, may include fewer synthetic steps and may produce the ent-Shi ketone catalyst in higher yields, relative to known methods. In some cases, the ent-Shi ketone catalyst may advantageously be produced in relatively large amounts, when performing a single iteration of a synthetic scheme. For example, carrying out the synthetic scheme shown in FIG. 1B one time may produce the ent-Shi ketone catalyst in relatively large quantities (e.g., greater than 10 grams). In some embodiments, the method may produce a catalyst (e.g., the ent-Shi catalyst) in an amount of 10 grams or greater, 20 grams or greater, 30 grams or greater, 40 grams or greater, 50 grams or greater, 60 grams or greater, 70 grams or greater, 80 grams or greater, 90 grams or greater, 100 grams or greater, 150 grams or greater, or, in some cases, 200 grams or greater, based upon a single run of a particular synthetic scheme. In one set of embodiments, the ent-Shi ketone catalyst may be produced in quantities ranging from about 50 grams to about 60 grams, based upon a single run of a particular synthetic scheme.

Some embodiments involve reacting a compound of Formula (I), (I)

wherein:

$R^1$ and $R^2$ can be the same or different and each can be hydrogen, alkyl, or aryl, provided that when one of $R^1$ and $R^2$ is hydrogen, the other is alkyl or aryl;

R³ is a protecting group;

R⁴ is a protecting group that can be removed in the presence of an acid; and

R⁵, R⁶, R⁷, and R⁸ can be the same or different and each can be hydrogen, alkyl, or aryl, to produce a compound of Formula (II),

(II)

In some embodiments, R¹ and R² are alkyl; and R⁵, R⁶, R⁷, and R⁸ are each hydrogen.

In one set of embodiments, the compound of Formula (I) has the structure,

In one set of embodiments, the compound of Formula (II) has the structure,

In some embodiments, the compound of Formula (I) may include at least one protecting group. For example, R³ and R⁴ may each comprise a silicon-containing protecting group. In some embodiments, the protecting group is trimethylsilyl (TMS), tributylsilyl (TBS), tert-butyldiphenylsilyl (TBDPS), tert-butyldimethylsilyl (TBDMS), triisopropylsilyl (TIPS), [2-(trimethylsilyl)ethoxy]methyl (SEM), trimethylsilyl triflate, triethylsilyl triflate, or tri-t-butylsilyl triflate. In one set of embodiments, the protecting group is tributylsilyl (TBS). In some cases, the protecting group may be capable of being removed in the presence of an acid.

The phrase "protecting group" as used herein refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

In some embodiments, conversion of a compound of Formula (I) to a compound of Formula (II) may be performed in a one-pot reaction. The term "one-pot" reaction is known in the art and refers to a chemical reaction which can produce a product in one step which may otherwise have required a multiple-step synthesis. One-pot procedures may eliminate the need for isolation (e.g., purification) of intermediates and additional synthetic steps while reducing the production of waste materials (e.g., solvents, impurities). Additionally, the time and cost required to synthesize such compounds can be reduced. For example, one or more chemical transformations may occur in a single reaction vessel to convert of a compound of Formula (I) to a compound of Formula (II), as described more fully below.

In some embodiments, the method may involve exposure of a compound of Formula (I) to an acid. As used herein, an "acid" refers to any species capable of acting as a source of at least one proton. Examples of acids include, but are not limited to, hydrochloric acid, hydrobromic acid, hydrofluoric acid, hydroiodic acid, hypochloric acid, chloric acid, perchloric acid, periodic acid, sulfuric acid, fluorosulfuric acid, nitric acid, phosphoric acid, hexafluorophosphoric acid, chromic acid, methanesulfonic acide, ethanesulfonic acid, benzenesulfonic acid, p-toluenesulfonic acid, trifluoromethanesulfonic acid, nitric acid, acetic acid, citric acid, formic acid, and the like. In some embodiments, the acid may be perchloric acid (HClO₄).

The acid may be provided as an aqueous solution comprising at least 1%, at least 10%, at least 20%, at least 30%, at least 40%, at least 50%, at least 60%, at least 70%, at least 80%, or, in some cases, at least 90% acid. In some embodiments, the acid may be added to the reaction mixture as a solution comprising about 50% to about 80% acid, about 60% to about 80% acid, or, about 70% to about 80% acid. In some embodiments, the acid may be added to the reaction mixture as a solution comprising 70% acid.

The compound of Formula (I) may be exposed to the acid under reaction conditions suitable for use in a particular application. In some embodiments, the reaction mixture may be maintained at any temperature from about −78° C. to about 200° C. In some embodiments, the acid may be added to the reaction mixture at relatively lower temperatures. For example, the reaction mixture may be maintained at any temperature from about −78° C. to about room temperature. In some embodiments, the reaction mixture may be maintained at about room temperature or lower, at about 15° C. or lower, at about 10° C. or lower, at about 5° C. or lower, or, at about 0° C. or lower. In one set of embodiments, the reaction mixture may be maintained at about 0° C.

Exposure of a compound of Formula (I) to an acid may result in one or more chemical transformations, including addition of a nucleophile to a carbonyl, removal/addition of protecting group(s), isomerization of protecting group(s), and the like. For example, exposing compound 4 to perchloric acid results in transformation of compound 4 to compound 5. (FIG. 1B) Without wishing to be bound by theory, FIG. 2 shows a proposed mechanism for conversion of compound 4 to compound 5, involving multiple chemical transformations upon exposure to compound 4 to an acid. In some cases, the compound may undergo acid-catalyzed isomerization, such that a protecting group (e.g., cyclic ketal) may moved to a different portion of the compound, as shown in step (a) of FIG. 2. For example, the cyclic ketal of compound 4 may be fully removed from compound 4 upon exposure to acid, and a new cyclic ketal may be formed at a different location of compound 4. Alternatively, the cyclic ketal in compound 4 may be partially removed from compound 4 (e.g., only one carbon-oxygen bond of the cyclic ketal may be cleaved) and may migrate to a different location of compound 4, upon exposure to acid. Upon isomerization of the cyclic ketal, the compound may then cyclize via addition of hydroxyl group to the carbonyl, as shown in step (b) of FIG. 2. Subsequent removal and/or addition of protecting groups at various locations may then produce compound 5, as shown in steps (c)-(e) of FIG. 2.

In some cases, the method may involve the subsequent step of neutralizing the acid. This may be performed, for example, by exposing the reaction mixture to a base. Bases suitable for use in the invention include those having sufficient pKa values to neutralize (e.g., deprotonate) an acidic reagent present within the reaction mixture. In general, a variety of bases may be used in practice of the present invention. Examples of bases include, but are not limited to, alkoxides such as sodium t-butoxide, an alkali metal amide such as sodium amide, lithium diisopropylamide or an alkali metal bis(trialkylsilyl) amides such as lithium bis(trimethylsilyl)amide or sodium bis(trimethylsilyl)amide, a tertiary amine (e.g. triethylamine, trimethylamine, Et(i-Pr)$_2$N, Cy$_2$MeN, 4-(dimethylamino)pyridine (DMAP), 2,6-lutadine, N-methylpyrrolidine (NMP), quinuclidine, and the like), 1,5-diazabicycl[4.3.0]non-5-ene (DBN), 1,5-diazabicyclo[5.4.0]undec-5-ene (DBU), ammonium salts (e.g., ammonium hydroxide), alkali and alkaline earth carbonates, alkali and alkaline earth bicarbonates, alkali and alkaline earth hydroxides, alkali and alkaline earth hydrides, (e.g. NaH, LiH, KH, K$_2$CO$_3$, Na$_2$CO$_3$, Ti$_2$CO$_3$, Cs$_2$CO$_3$, K(Ot-Bu), Li(Ot-Bu), Na(Ot-Bu) K(OPh), Na(OPh)), and the like. In some embodiments, a solution of ammonium hydroxide may be added to the reaction mixture to neutralize, for example, HClO$_4$.

Other suitable bases include quinoline, optionally substituted with alkyl or aryl groups, isoquinoline, optionally substituted with alkyl or aryl groups, imidazole, optionally substituted with alkyl or aryl groups, thiazole, optionally substituted with alkyl or aryl groups, and oxazole, optionally substituted with alkyl or aryl groups. In the above compounds, preferred alkyl substitutents may be C$_{1-5}$ alkyl groups and preferred aryl substitutents may be C$_{6-20}$ aryl groups, such as phenyl, substituted phenyl, naphthyl, phenanthryl, and the like. The base may be added in solid form, or as a solution comprising a base (e.g., an aqueous solution). For example, the acid may be neutralized by exposure to an ammonium hydroxide solution.

In some cases, the method may comprise a protection or deprotection reaction. For example, the compound of Formula (I) may be exposed to a protecting group precursor, which may interaction with a portion of the compound to produce a compound comprising a protecting group. In some cases, the compound of Formula (I) may comprise at least one protecting group and may be exposed to conditions under which the protecting group may be at least partially removed. In some embodiments, the protecting group may be removed from the compound. In some embodiments, the protecting group may be partially removed from the compound. For example, the protecting group may be attached to the compound via at least two bonds, and one of the bonds may be cleaved during a deprotection step. Some embodiments may involve migration of a protecting group from one location of the compound to another, different location of the compound.

In some cases the protection or deprotection reaction may be performed in the absence of additional chemical transformations. In some embodiments, the protection or deprotection reaction may be performed simultaneously with another chemical transformation. For example, a compound of Formula (I) may be exposed to an acid and a protecting group precursor at the same time, and may undergo both removal/addition of a protecting group and addition of a nucleophile to a carbonyl.

Some embodiments involve exposure of a compound of Formula (I) to a species capable of forming an acetal or a ketal as a protecting group. As used herein, the terms "acetal" and "ketal" are given their ordinary meaning in the art and refer to carbonyl-protecting groups having the formula, wherein R$^a$, R$^b$, and R$^c$ are carbon-containing groups, R$^d$ is hydrogen in the case of an acetal, and R$^d$ is a carbon-containing group in the case of a ketal. In some cases, the species may be capable of forming a cyclic acetal or a cyclic ketal, i.e., where R$^a$ and R$^b$ are joined together to form a ring. In some embodiments, acetals may be produced by reacting an aldehyde species with an alcohol. In some embodiments, ketals may be produced by reacting a ketone species with an alcohol.

In some embodiments, the compound of Formula (I) may comprise at least one hydroxyl group capable of forming an acetal or a ketal upon exposure to an aldehyde species or a ketone species. For example, the compound may comprise two hydroxyl groups, each attached to adjacent atoms of the compound (e.g., a vicinal diol), which may react with a ketone species to form a cyclic ketal. In some embodiments, the ketone species may be acetone. As described herein, some embodiments may involve acid-catalyzed isomerization of a cyclic ketal.

In some embodiments, the compound of Formula (I) may be exposed to conditions suitable to remove one or more protecting groups. For example, the compound may comprise a silicon-containing protecting group and may be exposed to a fluoride-containing species capable of removing the silicon-containing protecting group from the compound. Examples of fluoride-containing species include, but are not limited to, sodium fluoride (NaF) and tetra-n-butylammonium fluoride (TBAF). In some cases, the compound may comprise a TBS group, which may then be removed upon exposure to, for example, TBAF.

In one set of embodiments, the act of reacting a compound of Formula (I) comprises (i) exposure to HClO$_4$ and acetone; (ii) exposure to ammonium hydroxide solution; and (iii) exposure to tetra-n-butylammonium fluoride (TBAF).

The method may further comprise exposing the compound of Formula (II) to an oxidant. As used herein, the terms "oxidant" or "oxidizing agent" are given their ordinary meaning in the art and refer to a species capable of oxidizing or increasing the oxidation number of a substrate. In some embodiments, the oxidant may be comprise a transition metal. For example, the oxidant may comprise ruthenium. Examples of oxidants include halogens (e.g., iodine), peroxides, sulfoxides, ozone, osmium tetroxide, ruthenium(III) trichloride, chlorite, chlorate, perchlorate, hexavalent chromium compounds, nitric acid, nitrous oxide, permanganate salts, and the like.

In one set of embodiments, the compound of Formula (II) is oxidized to produce the ent-Shi catalyst, i.e., a compound having the structure, In some embodiments, the method may further comprising synthesizing a compound of Formula (I). In some embodiments, the compound may be synthesized via an aldol reaction. In some embodiments, the compound may be synthesized via an asymmetric aldol reaction. The method may involve performing an aldol reaction between an aldehyde species having the formula, wherein $R^1$ and $R^2$ can be the same or different and each can be hydrogen, alkyl, or aryl, provided that when one of $R^1$ and $R^2$ is hydrogen, the other is alkyl or aryl; and $R^5$ and $R^6$ can be the same or different and each can be hydrogen, alkyl, or aryl, and a carbonyl species having the formula, wherein $R^3$ is a protecting group;

$R^4$ is a protecting group that can be removed in the presence of an acid; and $R^7$ and $R^8$ can be the same or different and each can be hydrogen, alkyl, or aryl.

In some embodiments, the aldehyde species has the following structure,

In some embodiments, the carbonyl species has the following structure,

The aldol reaction may be performed under conditions suitable for use in a particular application. In some embodiments, the aldol reaction may be performed in the presence of one or more asymmetric (e.g. chiral) species capable of enhancing the formation of a particular desired product. For example, the aldol reaction may be performed in the presence of a chiral catalyst, chiral auxiliary, and/or chiral substrates. Those of ordinary skill in the art would be able to select the appropriate chiral species to produce a particular, desired product (e.g., syn aldol product, anti aldol product). In some embodiments, a syn aldol product may be the desired product. In some embodiments, an anti aldol product may be the desired product. In an illustrative embodiment, an asymmetric aldol reaction may be performed in the presence of O-tert-butyl-L-threonine.

The aldol reaction may be performed in the presence of one or more solvents, including organic solvents, aqueous solvents, and combinations thereof. In some embodiments, the solvent may be a polar aprotic solvent. Examples of polar aprotic solvents include N-methylpyrrolidinone (NMP), dimethylformamide (DMF), dimethylacetamide, and dimethyl sulfoxide, and the like.

In some embodiments, the aldol reaction mixture may be maintained at any temperature from about −78° C. to about 200° C. For example, the aldol reaction mixture may be maintained at any temperature from about −78° C. to about 50° C. In some embodiments, the aldol reaction mixture may be maintained at about 50° C. or lower, at about 30° C. or lower, at about 10° C. or lower, at about 5° C. or lower, or, at about 0° C. or lower. In one set of embodiments, the reaction mixture may be maintained at about room temperature.

Upon reaction, the contrast agent may be subjected to one or more purification steps. Purification and isolation may be performed using methods known to those skilled in the art, including separation techniques like chromatography, or combinations of various separation techniques as are known the art. In one embodiment, high performance liquid chromatography (HPLC) may be used with a solvent, or mixture of solvents, as the eluent, to recover the product. In some cases, the eluent may include a mixture of water and acetonitrile, such as a 45:55 water:acetonitrile mixture. The content of water may vary from, for example, about 1% to about 50%. In some cases, HPLC may be performed using a C18 column.

Any of the compounds or intermediates described herein product may be further processed using one or more purification techniques. Purification and isolation may be performed using methods known to those skilled in the art, including separation techniques like chromatography, recrystallization, distillation, or combinations of various separation techniques as are known the art. In some cases, the compound or intermediate may be purified using column chromatography. Any solvent, or mixture of solvents, may be uses the eluent to recover the product. In some cases, the eluent may include hexane, ethyl acetate, and/or a mixture of hexane and ethyl acetate, such as a 1:1 hexane:ethyl acetate mixture, a 2:1 hexane:ethyl acetate mixture, a 20:1 hexane:ethyl acetate mixture, or the like.

In some embodiments, a compound or intermediate may be purified using recrystallization, a process which may be repeated until desired purity of product is obtained. In one embodiment, the compound or intermediate is recrystallized at least once, two times, three times, or four or more times to achieve the desired level of purity. For example, the compound or intermediate may be obtained at purities of greater than or equal to 50%, 80%, 85%, 90%, 95%, 97%, 98%, 98.5%, 99.8%. Recrystallization may be achieved using a single solvent, or a combination of solvents. In some cases, recrystallization is achieved by dissolving the compound or intermediate in a solvent such as hexane at elevated temperatures, and then cooling the solution to produce a precipitate. For example, the compound may be recrystallized from hexane.

Figure 1A:
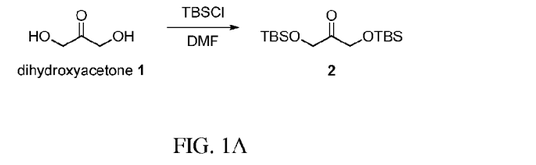
FIG. 1A shows the preparation of compound 2, a TBS-protected dihydroxyacetone.
Figure 1B:
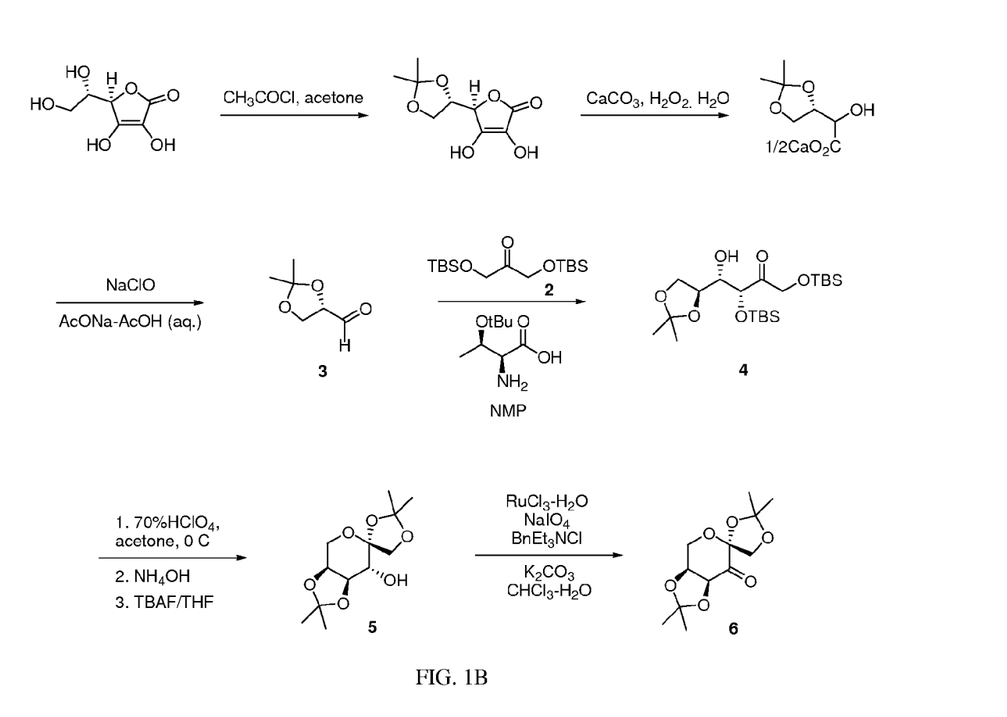
FIG. 1B shows the synthesis of the ent-Shi ketone.
Figure 2:
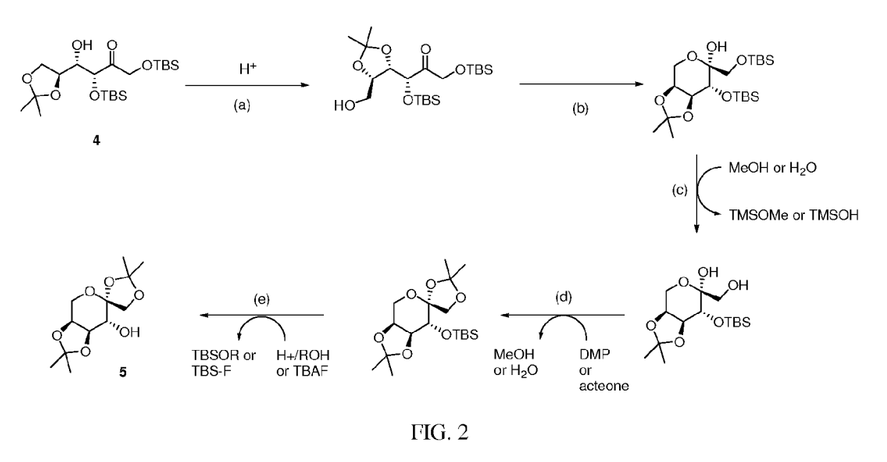
FIG. 2 shows a proposed mechanism for synthesis of an intermediate compound in the synthesis of the ent-Shi ketone.

FIG. 1B shows an illustrative embodiment, wherein ent-Shi ketone 6 (the ent-Shi ketone catalyst) is synthesized from L-ascorbic acid. As shown in FIG. 1B, L-ascorbic acid may be converted to (S)-glyceraldehyde 3, using the methods described in U.S. Publication No. 2007/0073068, the contents of which are incorporated herein by reference in its entirety for all purposes. An asymmetric aldol reaction may then be performed between (S)-glyceraldehyde 3 and compound 2, in the presence of O-tert-butyl-L-threonine and NMP, to produce aldol compound 4. Compound 4 may then be reacted as described herein. In one set of embodiments, the act of reacting compound 4 comprises (i) exposure to $HClO_4$ and acetone; (ii) exposure to ammonium hydroxide solution; and (iii) exposure to tetra-n-butylammonium fluoride (TBAF), to produce compound 5, which may then be oxidized to produce ent-Shi ketone 6.

In some embodiments, the ent-Shi ketone catalyst may be synthesized from (S)-glyceraldehyde in three steps with an overall yield of at least 10%, at least 20%, or at least 30%. In some cases, the ent-Shi ketone catalyst may be synthesized from (S)-glyceraldehyde in three steps with an overall yield of about 35%. In some embodiments, the ent-Shi ketone catalyst may be synthesized from L-ascorbic acid in six steps with an overall yield of at least 5%, at least 10%, or at least 13%. In some cases, the ent-Shi ketone catalyst may be synthesized from L-ascorbic acid in six steps with an overall yield of about 13.2%.

Some embodiments provide novel compounds or intermediates. In some case, compositions are provided comprising a compound having a structure as in Formula (I):

wherein:

$R^1$ and $R^2$ can be the same or different and each can be hydrogen, alkyl, or aryl, provided that when one of $R^1$ and $R^2$ is hydrogen, the other is alkyl or aryl;

$R^3$ is a protecting group;

$R^4$ is a protecting group that can be removed in the presence of an acid; and

$R^5$, $R^6$, $R^7$, and $R^8$ can be the same or different and each can be hydrogen, alkyl, or aryl.

In some embodiments, the compound has the following structure,

In some embodiments, $R^3$ and $R^4$ each comprise a silicon-containing protecting group, such as trimethylsilyl (TMS), tributylsilyl (TBS), tert-butyldiphenylsilyl (TBDPS), tert-butyldimethylsilyl (TBDMS) triisopropylsilyl (TIPS), [2-(trimethylsilyl)ethoxy]methyl (SEM), trimethylsilyl triflate, triethylsilyl triflate, or tri-t-butylsilyl triflate.

In some embodiments, the compound of Formula (I) has the structure,

In other embodiments, compositions comprising a compound having a structure as in Formula (II):

wherein:

$R^1$ and $R^2$ can be the same or different and each can be hydrogen, alkyl, or aryl, provided that when one of $R^1$ and $R^2$ is hydrogen, the other is alkyl or aryl; and $R^5$, $R^6$, $R^7$, and $R^8$ can be the same or different and each can be hydrogen, alkyl, or aryl, are provided.

In one set of embodiments, the compound has the following structure,

Suitable silicon compounds or silicon-containing compounds which may be used in methods of the invention may include those which are capable of forming a covalent bond with an oxygen atom. For example, the silicon-containing compound may form a covalent bond with an oxygen atom to form a silyl ether. In some embodiments, the silicon compound has the formula $R^3SiX$, wherein $R^3$ can be optionally substituted alkyl, optionally substituted cycloalkyl, optionally substituted aryl, optionally substituted heteroaryl, and X can be halide, triflate, or the like. In some embodiments, the silicon compound is trimethylsilyl (TMS), tributylsilyl (TBS), tert-butyldiphenylsilyl (TBDPS), tert-butyldimethylsilyl (TBDMS) triisopropylsilyl (TIPS), [2-(trimethylsilyeethoxy]methyl (SEM), trimethylsilyl triflate, triethylsilyl triflate, or tri-t-butylsilyl triflate. In some embodiments, the Solvents which may be used in methods of the invention include inert solvents such as benzene, p-cresol, toluene, xylene, diethyl ether, glycol monomethyl or dimethyl ether, petroleum ether, hexane, cyclohexane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, mixtures thereof, or the like. Preferred solvents may include benzene, toluene, xylene, ether, hexane, petroleum ether, methylene chloride, chloroform, or tetrahydrofuran. In a particular embodiment, toluene is the preferred solvent.

The products which may be produced by methods of the present invention may undergo further reaction(s) to afford desired derivatives thereof. Such permissible derivatization reactions can be carried out in accordance with conventional procedures known in the art. For example, potential derivatization reactions include cleavage of the oxygen-silicon bond of a silyl ether of an allylic alcohol to afford the allylic alcohol. Suitable reagents which can cleave an oxygen-silicon bond to deprotect an alcohol are known, such as tetrabutylammonium fluoride (TBAF), for example.

As used herein, the term "reacting" refers to the forming of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s). A "stable, isolable compound" refers to isolated reaction products and does not refer to unstable intermediates or transition states.

In the compounds and compositions of the invention, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclohexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "alkenyl" and "alkynyl" refer to unsaturated aliphatic groups analogous in length and possible substitution to the alkyls described above, but that contain at least one double or triple bond respectively.

The terms "heteroalkenyl" and "heteroalkynyl" refer to unsaturated aliphatic groups analogous in length and possible substitution to the heteroalkyls described above, but that contain at least one double or triple bond respectively.

As used herein, the term "halogen" or "halide" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, heteroalkyl, aryl, or heteroaryl, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the The terms "heteroaryl" refers to aryl groups comprising at least one heteroatom as a ring atom.

The term "heterocycle" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "amine" and "amino" are art-recognized and refer to both unsubstituted and substituted amines, e.g., a moiety that can be represented by the general formula: N(R')(R")(R'") wherein R', R", and R'" each independently represent a group permitted by the rules of valence. An example of a substituted amine is benzylamine.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and can not be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $-CF_3$, $-CN$, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, aralkyloxyalkyl, and the like.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Con- sisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

EXAMPLES

Example 1 dihydroxyacetone

The following example describes a procedure for the TBS-protection of dihydroxyacetone (Preparation of Compound 2), as described in Sodeoka et al., *J. Am. Chem. Soc.* 1990, 112, 4906, the contents of which are incorporated herein by reference. To a solution of dihydroxyacetone 1 (250.00 g, 2.78 mol) and imidazole (472.34 g, 6.94 mol; 2.5 equiv) in DMF (1250 mL) TBS-Cl (1045.70 g, 6.94 mol; 2.5 equiv) was added over about 40 min between 0 to 30° C. Then, the mixture was stirred at room temperature until dihydroxyacetone was disappeared (typical reaction time is 4 to 5 hours. Reaction progress was monitored by TLC.). After completion of the reaction, ice-water (1500 mL) was added to the reaction mixture and extracted with ethyl acetate (1500 mL). The aqueous layer was separated and organic layer was washed with water (1500 mL), then 20% NaCl aq. (1500 mL). The organic layer was evaporated to dryness and the residue was purified by distillation (bp. 135-138° C. at 3 mmHg) to give 2 as colorless oil (849.83 g, 96% yield).

Example 2

Compound 4 was synthesized according to the procedure described in Barbas et al., *Org. Lett.* 2007, 9, 3445, with slight modifications for large scale synthesis. A solution of (S)-glyceraldehyde 3 was prepared according to method described in U.S. Publication No. 2007/0073068, and used without purification. The solution of (S)-glyceraldehyde 3 (100 g (assumed net quantity), 768.4 mmol) and 2 (489.63 g, 1536.8 mmol; 2.0 equiv) in N-methylpyrolidone (142.5 mL) and water (7.5 mL), O-tert-butyl-L-threonine (26.93 g, 153.7 mmol; 0.2 equiv) was stirred at room temperature until 3 was no longer detectable by TLC (reaction time was about 24-72 hours and yield was about 70-95%; however, this may vary due to the quality and/or solubility of catalyst). This reaction mixture was diluted with n-hexane (2000 mL) and washed with water (1000 mL), water (500 mL), water (500 mL), 0.1M HCl aq. (500 mL), 5% NaHCO₃ aq. (500 mL), and 10% NaCl aq. (500 mL). The organic layer was evaporated to dryness and the residue was purified by silica gel column chromatography (silica gel 2 kg; n-hexane/ethyl acetate=200/1 (4020 mL), 100/1 (4040 mL), 50/1 (4080 mL), 20/1 (4200 mL), 10/1 (4400 mL), 4/1 (5000 mL) to give 4 as colorless oil (258.62 g, 75% yield).

Excess TBS-protected dihydroxyacetone 2 was recovered as colorless oil (282.00 g, 58% based on the initial amount), and can be re-used after distillation (90% yield).

Also, excess O-tert-butyl-L-threonine was also recovered by concentrating the 1st to 3rd aqueous layers and adding 2-PrOH (500 mL) to the residue. The mixture was stirred for 10 hours at room temperature, upon which a precipitate formed. The precipitate was filtered and washed with 2-PrOH to give O-tert-butyl-L-threonine as white powder (27.06 g, 53%).

Example 3

The following example describes the synthesis of compound 5. To a solution of aldol product 4 (238.46 g, 531.4 mmol) in acetone (1900 mL) and water (2.3 mL) 70% HClO$_4$ (7.63 g, 53.14 mmol) was added at 0° C. and stirred at the same temperature for 1.5 hour. The reaction mixture was quenched with 28% NH$_4$OH (7.4 mL, 53.14 mmol). A 1M tetrabutyl-ammonium fluoride in THF solution (1062.8 mL, 1062.8 mmol, 2 equiv) was then added, and the mixture was stirred for 9 hours at room temperature. After removal of solvent, the residue was diluted with ethyl acetate (2400 mL) and washed with water (1200 mL) and 20% NaCl aq. (1200 mL). The aqueous layers were reextracted with ethyl acetate (2400 mL), and the combined organic layers were dried over anhydrous magnesium sulfate. The solvent was evaporated dryness and the remaining residue was purified by silica gel column chromatography (silica gel 1 kg; n-hexane/ethyl acetate=20/1 (4200 mL), 2/1 (3000 mL), 1/1 (4000 mL)) a to give white powder (130.15 g. 94.1%), which contained about 10-20% impurities. To this powder n-hexane (1440 mL) was added and refluxed until powder was dissolved. The solution was gradually cooled to 0° C., upon which a precipitate formed. The precipitate was filtered and washed with cold n-hexane (240 mL) to give ent-Shi alcohol 5 as white powder (87.07 g, 63%).

Example 4

The following example describes the preparation of ent-Shi ketone 6.

To a solution of Shi alcohol 5 (187.00 g, 718.5 mmol) in CHCl$_3$ (655 mL) and purified water (655 mL) RuCl$_3$.H$_2$O (4.47 g, 21.6 mmol, 3 mol %), NaIO$_4$ (230.51 g, 1077.7 mmol, 150 mol %), BnNEt$_3$Cl (8.18 g, 35.9 mmol, 5 mol %) and K$_2$CO$_3$ (14.89 g, 107.8 mmol, 15 mol %) were added and the mixture was refluxed for 1.5 hours with vigorous stirring. After starting material was disappeared, the mixture was cooled to room temperature. To this mixture 2-PrOH (47 mL) was added and stirred for 1 hour, then the mixture was filtered with celite and the residue was washed with CH$_2$Cl$_2$ (935 mL). The aqueous layer of the filtrate was removed and the organic layer was washed with 1M HCl aq. (560 mL), water (560 mL), 20% Na$_2$SO$_3$ aq. (560 mL), and 10% NaCl aq. (560 mL). The aqueous layers were reextracted with CH$_2$Cl$_2$ (560 mL). The combined organic layer was dried over anhydrous magnesium sulfate and concentrated to dryness. To the residue n-hexane (1580 mL) was added and the mixture was refluxed for 0.5 hours. Then the mixture was filtered and washed with hot n-hexane (300 mL). The filtrate was gradually cooled to −20° C. without stirring and stand for overnight. The precipitate was filtered and washed with cold n-hexane (370 mL) to give ent-Shi ketone 6 as a colorless needle (163.23 g, 88%).

What is claimed:

1. A method for synthesizing a catalyst, comprising:
reacting a compound of Formula (I), (I)

$R^5$ $R^6$ OH O
      $R^7$
          $R^8$,
O      OR$^3$ OR$^4$
 O
$R^1$ $R^2$ wherein:
$R^1$ and $R^2$ can be the same or different and each can be hydrogen, alkyl, or aryl, provided that when one of $R^1$ and $R^2$ is hydrogen, the other is alkyl or aryl;

$R^3$ is a protecting group;

$R^4$ is a protecting group that can be removed in the presence of an acid; and $R^5$, $R^6$, $R^7$, and $R^8$ can be the same or different and each can be hydrogen, alkyl, or aryl, to produce a compound of Formula (II), (II)

2. A method as in claim 1, wherein:
   $R^1$ and $R^2$ are alkyl; and
   $R^5$, $R^6$, $R^7$, and $R^8$ are each hydrogen.

3. A method as in claim 1, wherein $R^3$ and $R^4$ each comprise a silicon-containing protecting group.

4. A method as in claim 3, wherein the protecting group is trimethylsilyl (TMS), tributylsilyl (TBS), tert-butyldiphenylsilyl (TBDPS), tert-butyldimethylsilyl (TBDMS) triisopropylsilyl (TIPS), [2-(trimethylsilyl)ethoxy]methyl (SEM), trimethylsilyl triflate, triethylsilyl triflate, or tri-t-butylsilyl triflate.

5. A method as in claim 3, wherein the protecting group is tributylsilyl (TBS).

6. A method as in claim 1, wherein the compound of Formula (I) has the structure, 7. A method as in claim 1, wherein the compound of Formula (II) has the structure, 8. A method as in claim 1, wherein the act of reacting comprises exposure to an acid.

9. A method as in claim 8, wherein the acid is $HClO_4$.

10. A method as in claim 8, further comprising the act of neutralizing the acid.

11. A method as in claim 10, wherein the act of neutralizing comprises exposure to a base.

12. A method as in claim 10, wherein the act of neutralizing comprises exposure to an ammonium hydroxide solution.

13. A method as in claim 1, further comprising exposing the compound of Formula (I) to a species capable of forming an acetal or a ketal.

14. A method as in claim 1, further comprising exposing the compound of Formula (I) to a species capable of forming a cyclic ketal.

15. A method as in claim 1, further comprising exposing the compound of Formula (I) to a fluoride-containing species.

16. A method as in claim 15, wherein the fluoride-containing species is sodium fluoride (NaF) or tetra-n-butylammonium fluoride (TBAF).

17. A method as in claim 1, wherein the act of reacting comprises:
   (i) exposure to $HClO_4$ and acetone;
   (ii) exposure to ammonium hydroxide solution; and
   (iii) exposure to tetra-n-butylammonium fluoride (TBAF).

18. A method as in claim 1, further comprising the act of exposing the compound of Formula (II) to an oxidant.

19. A method as in claim 18, wherein the oxidant comprising a transition metal.

20. A method as in claim 18, wherein the oxidant comprises ruthenium.

21. A method as in claim 1, wherein the compound of Formula (II) is oxidized to produce a compound having the following structure, 22. A method as in claim 1, further comprising synthesizing a compound of Formula (I) via an aldol reaction.

23. A method as in claim 22, wherein the aldol reaction comprises:
   reacting an aldehyde species having the formula, with a carbonyl species having the formula.

24. A method as in claim 23, wherein the aldehyde species has the following structure, 25. A method as in claim 23, wherein the carbonyl species has the following structure,

* * * * *

UNITED STATES PATENT AND TRADEMARK OFFICE
CERTIFICATE OF CORRECTION

PATENT NO. : 8,680,303 B2  
APPLICATION NO. : 13/037060  
DATED : March 25, 2014  
INVENTOR(S) : Timothy F. Jamison et al.

Page 1 of 1

It is certified that error appears in the above-identified patent and that said Letters Patent is hereby corrected as shown below:

On the title page, enter the following item (60) below the Prior Publication Data section:

--Related U.S. Application Data

(60) Provisional application No. 61/309,067, filed on March 1, 2010.--

Signed and Sealed this  
Ninth Day of December, 2014

Michelle K. Lee  
*Deputy Director of the United States Patent and Trademark Office*